United States Patent [19]

Burns

[11] Patent Number: 4,616,425
[45] Date of Patent: Oct. 14, 1986

[54] MOISTURE MEASUREMENT APPARATUS AND METHOD

[75] Inventor: Stanley G. Burns, Ames, Iowa

[73] Assignee: Iowa State University Research Foundation, Ames, Iowa

[21] Appl. No.: 794,490

[22] Filed: Nov. 4, 1985

Related U.S. Application Data

[63] Continuation of Ser. No. 461,311, Jan. 28, 1983, abandoned.

[51] Int. Cl.[4] .............................................. F26B 1/00
[52] U.S. Cl. .......................................... 34/13.8; 34/48; 34/50; 34/89; 324/61 QS; 324/65 R
[58] Field of Search ................... 34/13.8, 43, 48, 50, 34/89; 324/61 QS, 65 R

[56] References Cited

U.S. PATENT DOCUMENTS

| | | | |
|---|---|---|---|
| 3,196,682 | 7/1965 | Johnson | 324/65 R |
| 3,295,042 | 12/1966 | Evalds et al. | 324/61 QS |
| 3,621,293 | 11/1971 | Heidtman | 34/48 |
| 3,807,055 | 4/1974 | Kraxberger | 324/65 R |
| 4,114,090 | 9/1978 | Poskitt | 324/61 QS |
| 4,259,633 | 3/1981 | Rosenau | 324/65 R |
| 4,270,085 | 5/1981 | Terada et al. | 324/65 R |
| 4,408,128 | 10/1983 | Fujita | 324/65 R |

Primary Examiner—Albert J. Makay
Assistant Examiner—David W. Westphal
Attorney, Agent, or Firm—Kent A. Herink; G. Brian Pingel

[57] ABSTRACT

Apparatus and method for measuring the moisture content of wood and paper products utilizing the dependency of the resistance or capacitance of such products upon moisture content. A resistance or capacitance-controlled oscillator circuit is completed by electrical connection to a product. Electrical connection of the resistance-controlled oscillator embodiment is accomplished by either application of a conducting contact grid pattern to a product or by forming a parallel plate probe incorporating the product therein. Electrical connection of the capacitance-controlled oscillator embodiment may also be accomplished by forming a parallel plate probe incorporating the product therein or by insertion of a plurality of conductive cylinders in parallel combination into flutes of a corrugated paperboard product when such a product is to be subject to measurement.

14 Claims, 10 Drawing Figures

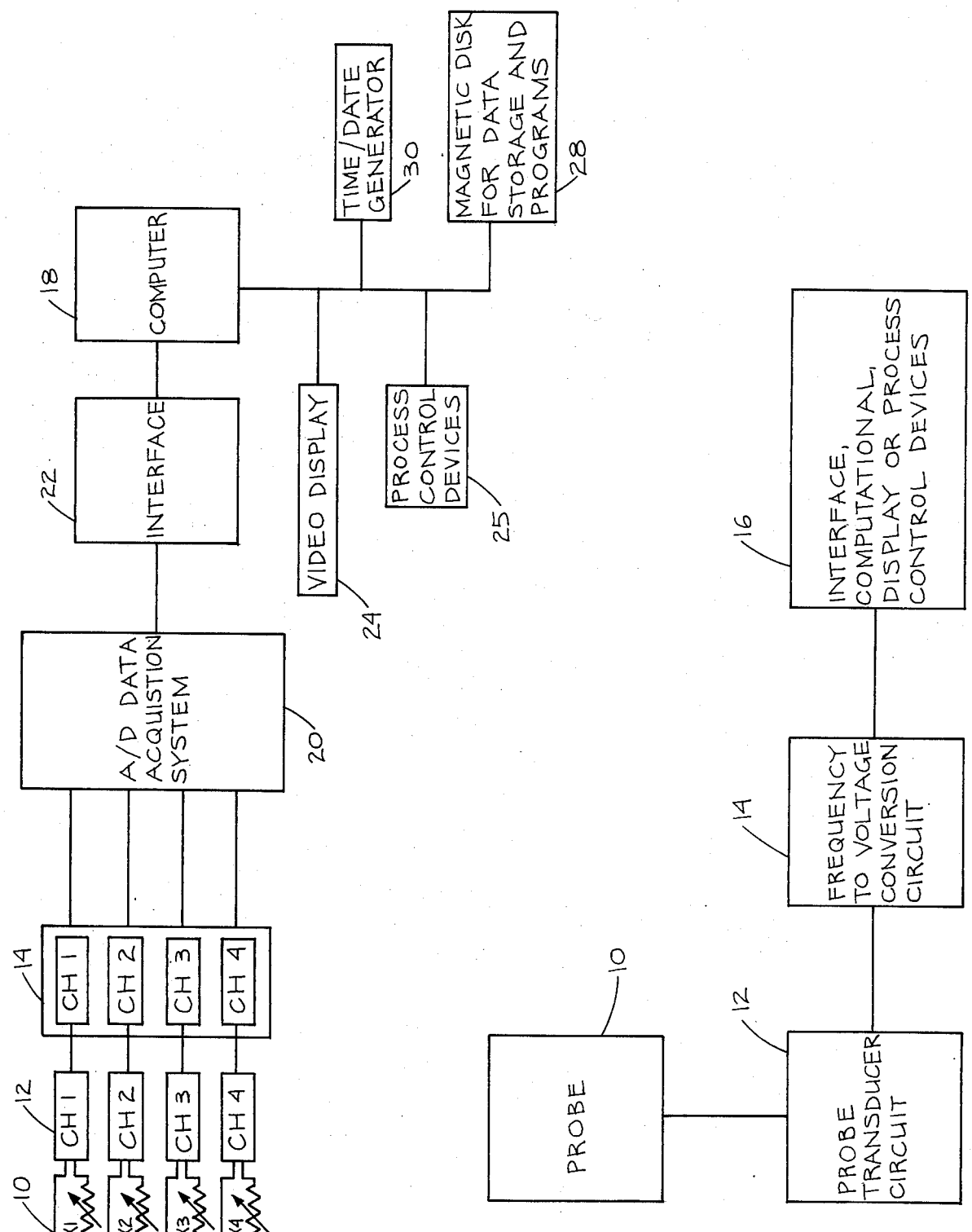

MOISTURE MEASUREMENT APPARATUS AND METHOD

GRANT REFERENCE

The invention described herein was made in the course of work under study no. 2-79-7/FP-1-0378 of the Forest Products Laboratory, Forest Service, U.S. Department of Agriculture.

This is a continuation of application Ser. No. 461,311, filed Jan. 28, 1983, now abandoned.

BACKGROUND OF THE INVENTION

1. Field of the Invention

This invention relates generally to an apparatus and method for determining the moisture content of wood and paper products, and more specifically, to an apparatus and method utilizing a resistance or capacitance-controlled oscillator circuit integrally incorporating in the circuit the wood or paper product sample.

2. Description of the Prior Art

The measurement of the moisture content of wood and paper products is relevant to many aspects of the wood and paper industry as well as to users of wood and paper products. Certain physical characteristics of such products directly relate to moisture content of the product. Therefore, manufacturing processes involving these products must be adjusted in accordance with the moisture content of the products. While changes in physical characteristics of products in relation to changes in the moisture content of the products are generally well known, there previously has existed no convenient and reliable apparatus or method for quickly and non-destructively determining the product's moisture content in an assembly-line setting or during long-term storage.

Several methods and devices have been used in the past to measure the moisture content of wood and paper products. One such method is to remove a sample portion of the product, weigh the test sample, heat the sample in an oven to drive off the moisture, then re-weigh the dry sample. The change in weight of the sample divided by the weight of the "wet" sample before drying gives the moisture content of the product. This method requires a large amount of time and is not completely accurate primarily as a result of changes in the moisture content of the test sample during the time between removal from the product and drying.

Another method for testing the moisture content of a product is described in the Rosenau U.S. Pat. No. 4,259,633. Rosenau discloses a method of inserting metal pins into a product and passing a direct current voltage through the sample. Owing to the fact that the resistance of wood and paper products varies with the moisture content of the products, the amount of current conducted by the sample at a given voltage generally corresponds to a particular level of moisture. However, in the Rosenau method, electrolytic polarization effects create a reverse voltage which can introduce a large degree of error into the measurement. Direct current measurement techniques also have inherent problems with zero level drift and stray charges which become especially troublesome when trying to measure the relatively high resistances characteristically found in wood and paper products.

Still another method for measuring the moisture content of wood and paper products includes the subjection of the products to microwave or infrared radiation. This method determines the moisture content of the sample by measuring the absorbtive loss in the impinging radiation after passing through the product and calculating the amount of moisture which would cause such a degree of loss in radiation. Although this method may be accurate, it requires rather elaborate and sensitive equipment that is not easily transported or inexpensively operated and maintained. Also, access must be had to both sides of the product to be measured. Consequently, it could not be used where sources of moisture other than the product to be measured may be interposed in the measurement path. In addition, this method affects the moisture content of the product since the microwave radiation heats the product, thereby driving off moisture. The microwave radiation method is therefore unsuited for monitoring time dependent responses of products to the environment.

It is therefore an object of this invention to provide a moisture detector for wood or paper products which employs a resistance or capacitance controlled oscillator circuit integrally including in the circuit the wood or paper product in order to measure the moisture content of the product, thereby overcoming the problems posed in the prior art including electrolytic polarization and zero level direct current drift, as found in detectors using direct current voltage.

It is another object of the invention to provide a moisture detector for wood or paper products capable of measuring the moisture-dependent resistance or capacitance of such products in spans comprising more than five orders of magnitude and automatically compressing the data through use of a resistance or capacitance-controlled oscillator circuit having a response logarithmically related to the measured resistance or capacitance.

It is a further object of the invention to provide a moisture detector for wood or paper products utilizing probes designed to enhance the effective measured resistance or capacitance and further designed to reduce errors due to fringing electrical fields and relative placement of the probes on the wood or paper products.

It is another object of the invention to provide a moisture detector for wood or paper products which is easily transportable and easily installed in areas difficult to reach with other detecting apparatus.

It is a further object of the invention to provide a moisture detector for wood or paper products which enables very rapid and accurate determination of the moisture content of the products.

It is another object of the invention to provide a moisture detector for wood or paper products which includes a probe and a resistance or capacitance controlled oscillator circuit to monitor the moisture content of the product over a long period of time without excising or destroying a portion of the product for moisture assay and without materially affecting the moisture content of the product such as experienced with the moisture assay and microwave methods described with reference to the prior art.

It is yet another object of the invention to provide a moisture detector for wood or paper products which includes a probe permanently applied to the surface of the product for measuring the moisture-dependent resistance or capacitance of the product through incorporation of the probe in a resistance or capacitance controlled oscillator circuit, thereby making the wood or paper product an integral component of the circuit.

It is a further object of the invention to provide a moisture detector for corrugated wood or paper products which includes a plurality of paired electrodes inserted into flutes of the corrugated product, thereby measuring the moisture-dependent dielectric constant of the product using a capacitance controlled oscillator circuit integrally comprised of the corrugated product.

BRIEF SUMMARY OF THE INVENTION

The instant invention includes a probe integrally comprised of the wood or paper product to be measured and a resistance or capacitance controlled oscillator connected to the probe. The wood or paper product thereby becomes a part of the oscillator circuit and determines the frequency at which the circuit oscillates. The output signal from the oscillator is then converted to a direct current voltage by a frequency-to-voltage conversion circuit. Following the conversion voltage level variations are sensed to produce an indication of the moisture content of the product as reflected by the voltage level which is, in turn, dependent upon the output frequency of the oscillator circuit comprised in part by the product being measured. In addition to indication of the moisture content it is contemplated that the sensed voltage level may also be used to initiate corrective changes in the environment in response to such measurement.

One probe of the invention includes a surface-applied conducting grid having two conductive elements and connection sites for electrically coupling the grid to the remainder of the oscillator circuit. A second probe is formed by applying a conductive material to opposite sides of the product for inclusion in the oscillator circuit. Still another probe for use as part of the oscillator circuit and primarily designed for use with a corrugated product, comprises a plurality of paired sets of conducting electrodes appropriately sized for insertion into the flutes of the corrugated product.

BRIEF DESCRIPTION OF THE DRAWINGS

FIG. 1 is a block diagram representing the wood and paper moisture measurement system of the present invention.

FIG. 2 is a block diagram of the invention showing the use of 4 independent probes and associated circuitry for application in a preferred embodiment of the invention.

DETAILED DESCRIPTION OF A PREFERRED EMBODIMENT

Figure 5:
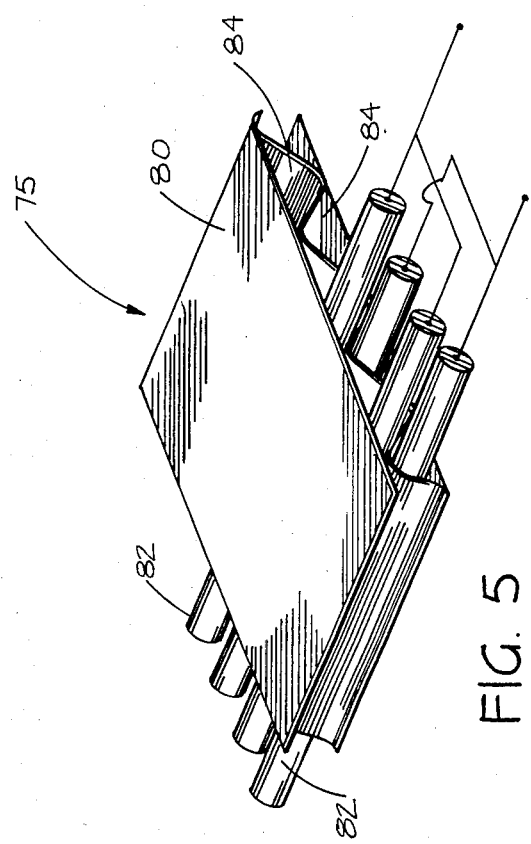
FIG. 5 is a perspective view of a corrugated sample having cavities into which have been inserted electrodes thereby forming another alternate probe of the invention.

FIG. 1 is a block diagram of the wood and paperboard direct moisture measurement system showing a probe 10 connected to a probe transducer circuit 12 which, in combination, generate an alternating current signal having a frequency representing and dependent upon the moisture content of the sample forming a part of the probe 10. A frequency to voltage conversion circuit 14 electronically converts the output frequency of the signal from circuit 12 into a proportional direct current voltage level.

As illustrated schematically in FIG. 1, the proportional direct current voltage level from the frequency-to-voltage conversion circuit 14 may be received by a wide variety of possible interface, computational, display or process control devices. Quite clearly, such a device may be as simple as a voltage sensitive meter scaled in humidity levels; it may be a conventional relay or other threshold detection device capable of altering the environmental humidity; or it may be a more complex analytical, display, or process control computer system.

A more detailed block diagram of a preferred embodiment of the invention employing a computer system for analysis, display, and process control, is shown in FIG. 2. In a preferred embodiment the interface, computational and display or process control devices 16 (see FIG. 1) include an Apple II ® computer 18 connected with the probes 10, here, a total of four probes illustrated schematically by $R_{x1}$, $R_{x2}$, $R_{x3}$, and $R_{x4}$, through an associated four channels, CH 1, CH 2, CH 3, and CH 4, of probe transducer circuits 12 and frequency-to-voltage conversion circuits 14 and through a data acquisition system 20 and a data acquisition system interface 22.

The computer 18 monitors the moisture content of the wood or paper products and permits a user to select the display of monitored values on a video display 24 or to record the values on a magnetic disk 28. Additionally, the computer 18 may initiate a responsive action to the measured moisture content, such as activating a dehumidifier, raising the temperature of the environs or operating other process control devices, represented schematically in FIG. 2 at 25. A time and date generator 30 is included to permit temporal analysis of the moisture measurements.

Figure 6:
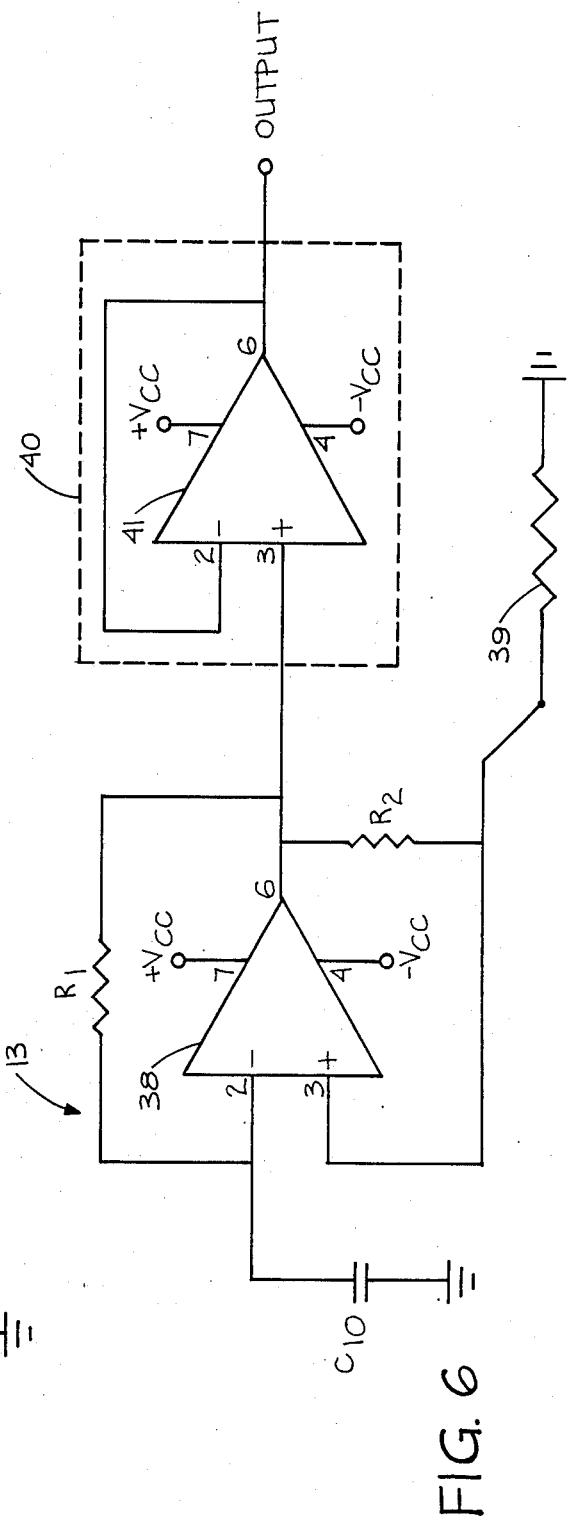
FIG. 6 is an electrical schematic diagram of the resistance-controlled oscillator circuit used in a preferred embodiment of the invention.

The probe transducer circuit, shown in FIG. 6, is a resistance-controlled oscillator circuit, generally at 13, including a resistive probe 39, representing either a surface-applied conducting grid probe 34 (see FIG. 3) or a parallel plate probe 36 (see FIG. 4), each of which will be further described below. The resistance-controlled oscillator circuit 13 is designed to accommodate moisture content measurements of wood or paper samples whose resistance may span five orders of magnitude. The logarithmic response of the output frequency of the oscillator 13 to the resistance of the probe 39 is given by:

$$\text{Output frequency} = \frac{1}{2R_1 C_{10} \ln\left(1 + \frac{2R_x}{R_2}\right)}$$

Where $R_x$ represents the resistance of the resistive probe 39. This logarithmic response effectively compresses the range of output frequencies to a more manageable scale and may yield accurate data at high resistance values encountered in relatively dry materials, which may be on the order of 100M ohms.

The resistance-controlled oscillator circuit 13 includes a BIFET operational amplifier 38. The BIFET operational amplifier 38 oscillates at a frequency characteristic of the RC circuit formed by reference capacitor $C_{10}$ and the resistance of the wood or paper product which forms part of the resistive probe 39. The resistive probe 39 in FIG. 6 could consist of the parallel plate probe 36 (see FIG. 4) or the surface-applied conducting grid probe 34 (see FIG. 3). The output frequency signal of the BIFET operational amplifier 38 is a zero volt centered square wave which is used to drive a unity gain buffer 40, including an operational amplifier 41. The unity gain buffer 40 provides an output signal which may reliably be conducted to the frequency-to-voltage conversion circuit 14 as schematically illustrated in FIG. 1.

Figure 8:
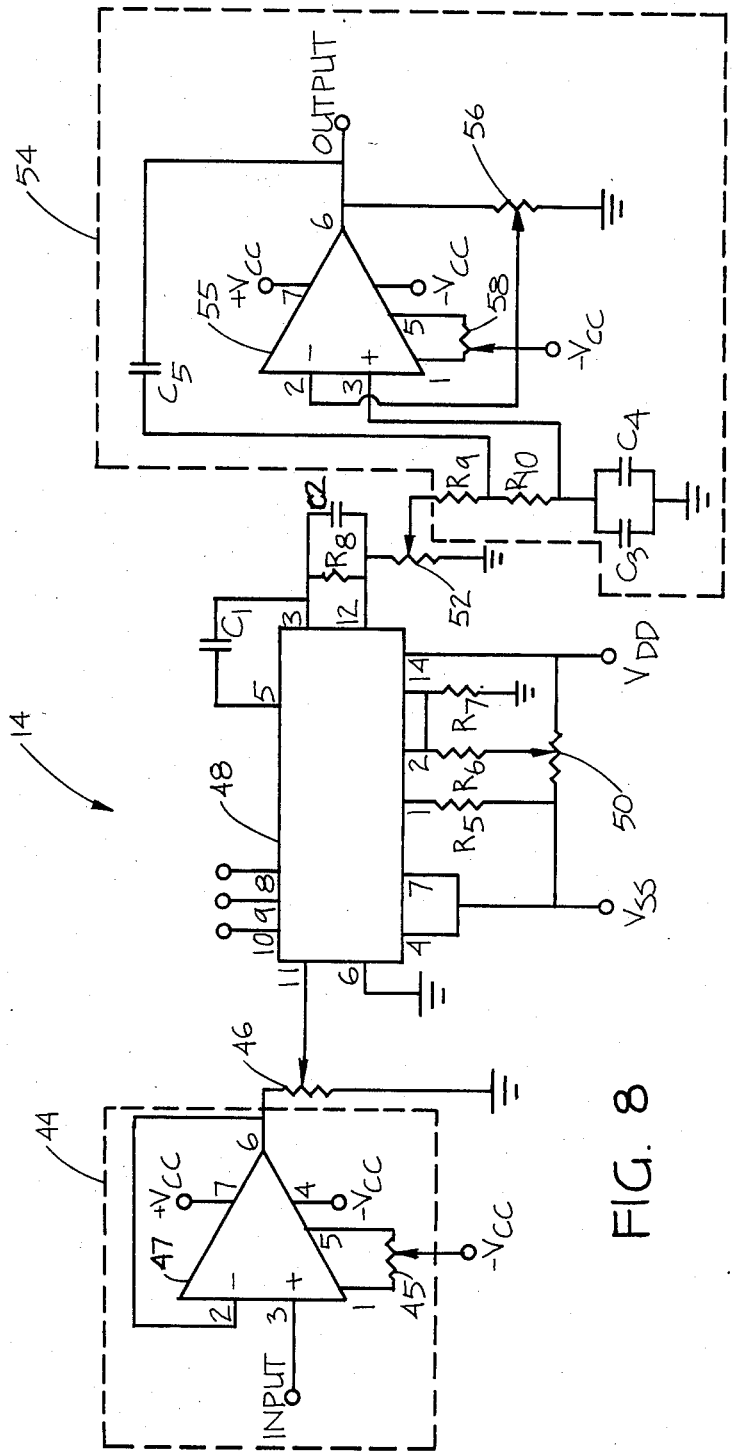
FIG. 8 is an electrical schematic diagram of the frequency-to-voltage conversion circuit used in a preferred embodiment of the invention.

A preferred embodiment of the frequency-to-voltage conversion circuit 14 is illustrated in detail in FIG. 8. The input signal received by the frequency-to-voltage conversion circuit 14 is buffered by a unity gain buffer 44. The buffer 44 is a part of the frequency-to-voltage conversion circuit 14 and includes an operational amplifier 47. An offset resistor 45 is provided for calibration and is used to adjust the output level of the buffer 44 to zero volts when the input signal to the frequency-to-voltage conversion circuit 14 is also at zero volts. An interstage coupling resistor 46 couples the buffer 44 to a frequency-to-voltage converter 48. The interstage coupling resistor 46 consists of a variable resistor and is used to adjust the over-all sensitivity of the conversion circuit 14.

The frequency-to-voltage converter 48 produces a direct current voltage level which is proportional to the frequency of the output signal of the buffer 44. Included in the frequency-to-voltage conversion circuit 14 is a second offset resistor 50 for calibration to adjust the direct current output voltage level of the frequency-to-voltage converter 48 to zero volts when the input frequency is zero Hertz.

A second interstage coupling resistor 52 couples the frequency-to-voltage converter 48 to a second order Butterworth filter 54. The filter 54 acts to remove residual frequency ripple in the signal and includes an operational amplifier 55. The Butterworth filter 54 also amplifies the signal by an amount determined by a variable resistor 56 included within the filter circuit 54 and which is adjusted in normal operation so that the output of the Butterworth filter 54 is 5 volts DC when the input frequency to the frequency-to-voltage converter 48 is 5,000 Hertz. Also included in the Butterworth filter 54 is a third offset resistor 58 for calibration to adjust the output of the Butterworth filter 54 to zero volts when the direct current level input to the Butterworth filter 54 is zero volts.

In general the two offset resistors 50 and 58 are adjusted so that the output of the Butterworth filter 54 is approximately 0.1 volts DC when the input frequency to the frequency-to-voltage converter 48 is 100 Hertz. Itteration in the adjustments of the two offset resistors 50 and 58 and the variable resistor 56 may be needed in order to optimize linearity in the frequency-to-voltage conversion circuit 14 and to optimize the scaling of the direct current output voltage level from zero volts at an input frequency of zero Hertz to 5 volts at an input frequency of 5,000 Hertz.

Figure 9:
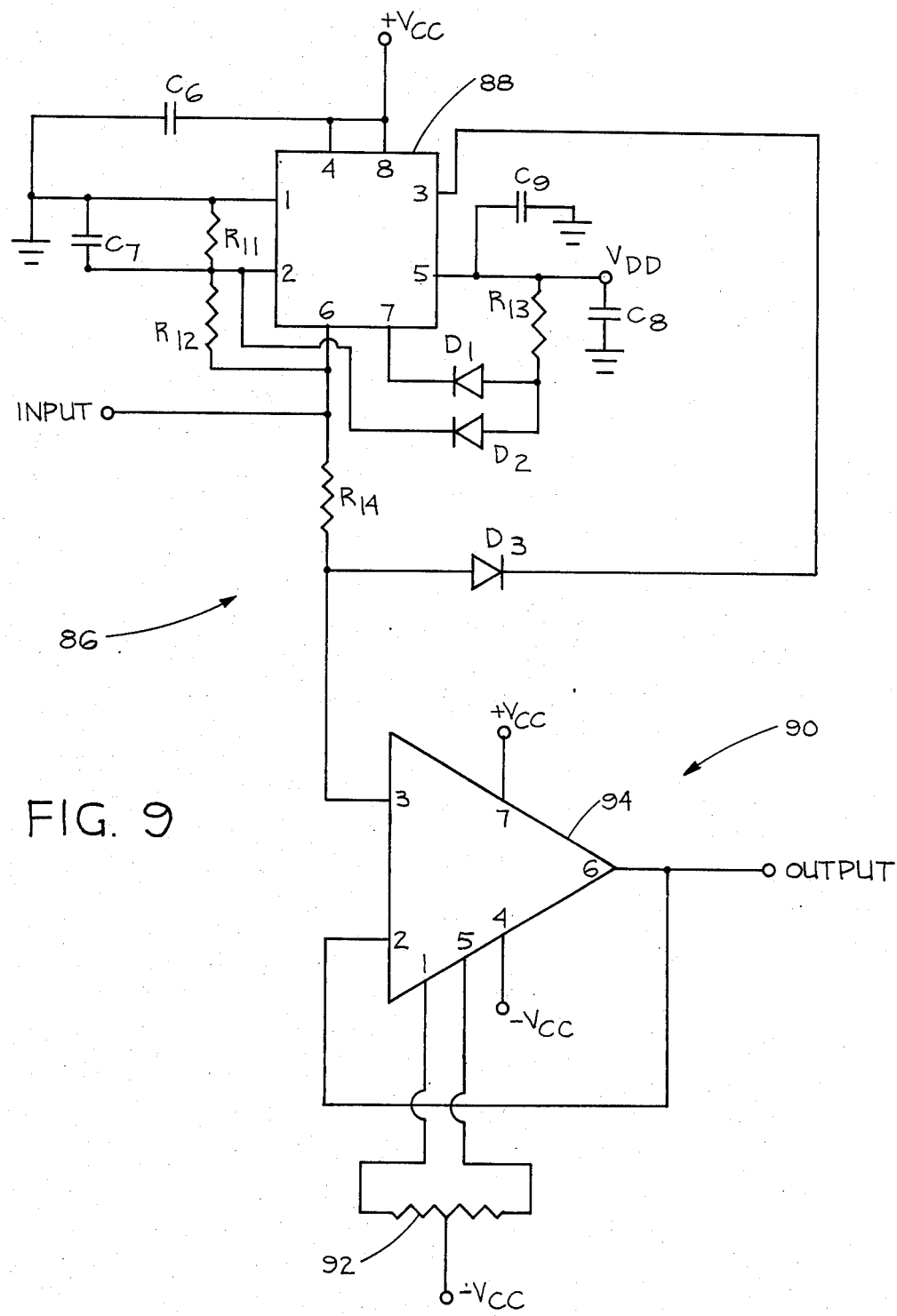
FIG. 9 is an electrical schematic diagram of an overlimit protection circuit used in a preferred embodiment of the invention.

In a preferred embodiment of the invention utilizing a computer 18 (see FIG. 2), the output DC voltage level of the Butterworth filter 54 is fed through an over-limit protection circuit, indicated generally at 86 in FIG. 9, which becomes a part of the frequency-to-voltage conversion circuit 14. The computer 18 may yield erroneous information if the DC voltage level received by the data acquisition system 20 is greater than 5 volts. The over-limit protection circuit 86 senses the output voltage level of the filter 54 and produces an output level of zero volts to the data acquisition system 20 when the output voltage level of the filter 54 is greater than 5 volts. The over-limit protection circuit 86 includes a threshold detector 88 and a unity gain buffer generally designated at 90. The buffer 90 includes an operational amplifier 94 and an offset resistor 92 for calibration to adjust the direct current voltage level output of the protection circuit 86 to zero volts when the input voltage level is zero volts.

The direct current output signal of the over-limit protection circuit 86 is received by a data acquisition system 20 depicted schematically in FIG. 2. The data acquisition system 20 is a conventional analog-to-digital converter which produces a digital signal corresponding to the analog direct current output voltage level of the frequency-to-voltage conversion circuit 14. It has been found that a National Semiconductor No. 6522 ADC-0816 data acquisition system, with appropriate connection for operation in the analog-to-digital conversion mode, provides acceptable conversion features in a working embodiment of the present invention.

Figure 10:
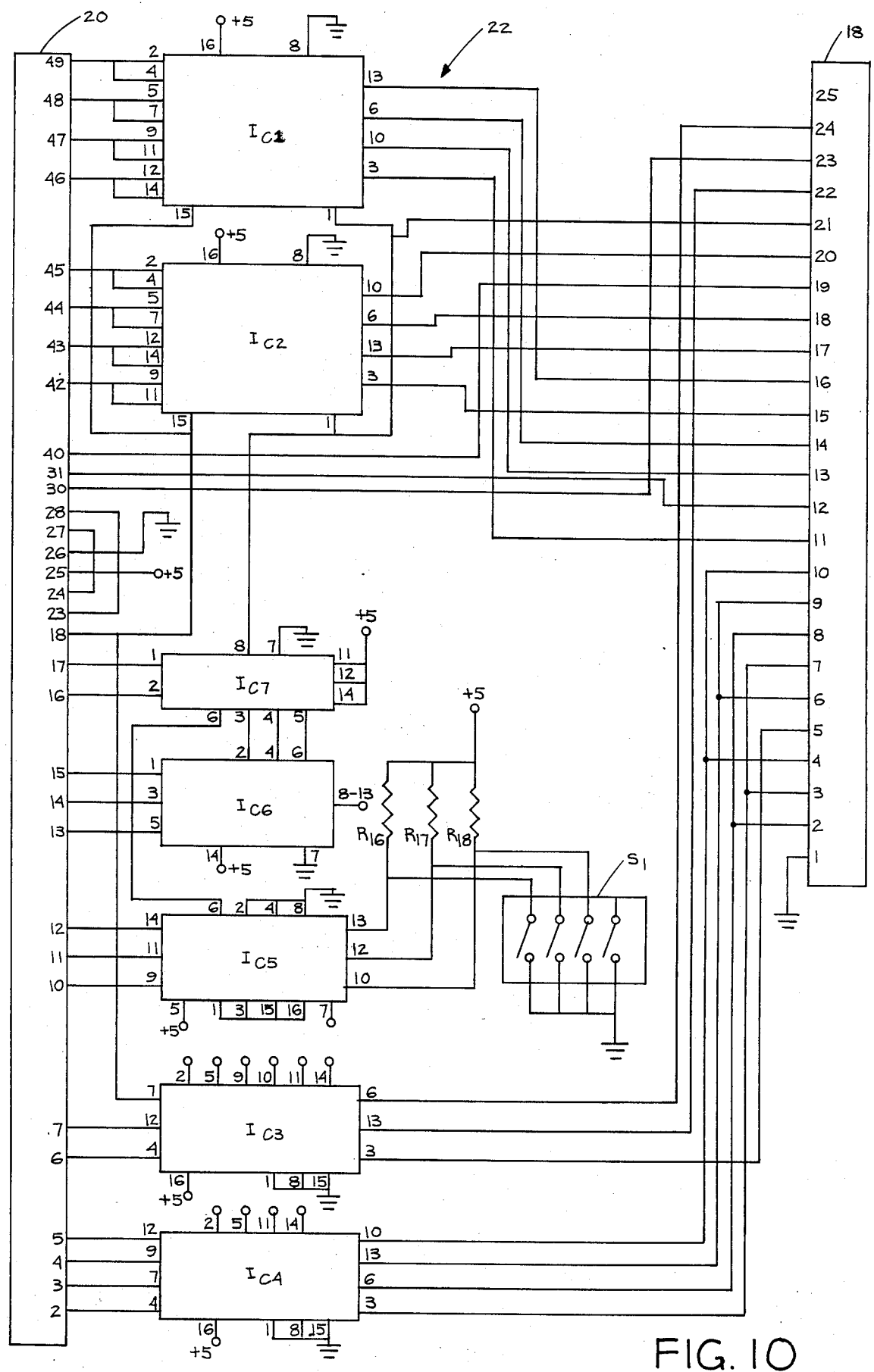
FIG. 10 is an electrical schematic diagram of the interface circuit used in a preferred embodiment of the invention.

An interface circuit 22 serves to condition and coordinate the digital signal of the data acquisition system 20 for acceptance by the computer 18. Although a wide range of commercially available interface apparatus could be used with the invention, a preferred embodiment of a custom-made interface circuit 22 is specifically designed, through selection of an appropriate setting of the four independent contacts of switch $S_1$, to define the respective "0" and "1" voltage levels for input to the computer 18. In the FIG. 10 embodiment, pin connection numbers of the data acquisition system 20 are for a National Semiconductor Device No. 6522 ADC-0816, as described above, and the pin connection numbers of the computer 18 are for an Apple II ® computer, as described above.

The computer 18 uses the information carried by the digital signal and its predetermined relationship to the moisture content of the sample to calculate the moisture content of the sample. The values calculated by the computer 18 may be selectively displayed on a video display 24 and stored on a magnetic disk 28, or any other display or data storage system known in the art. The computer may also initiate a response to the measured moisture content through appropriate environmental or mechanical response mechanisms or process control devices 25. A time and date generator 30 is included with the computer 18 and display and storage systems to allow the moisture content information to be displayed and stored together with the time and date it was taken, thereby enabling temporal analysis of the information. A source program listing as set out below in this specification has been found most desirable in the preferred embodiment of the invention.

Figure 3:
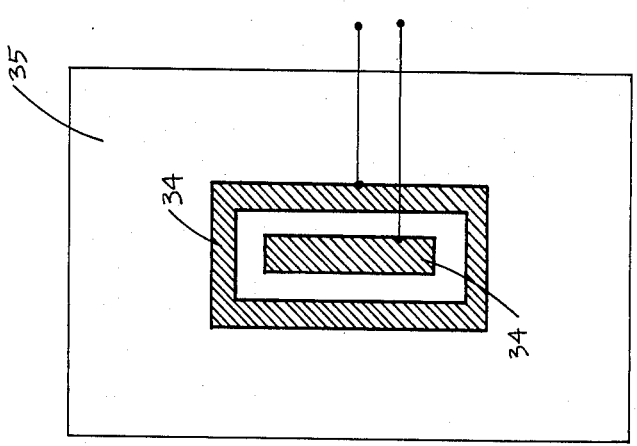
FIG. 3 is a plan view of a surface applied conducting grid probe of the invention.

A surface applied conducting grid probe 34 is shown in detail in FIG. 3. The grid probe 34 is applied directly to the surface of a wood or paper sample 35, preferably by painting a pattern with conducting silver paint in an acetone carrier. The optimum design and size of the pattern depends upon the physical characteristics of the sample, the location of the grid probe 34 on the sample and the desired frequency of the resistance-controlled oscillator 13 including the sample 35. It has been found that nested rectangles in the coaxial design of the grid probe 34 depicted in FIG. 3 give accurate and consistent results when used with the resistance-controlled oscillator circuit 13.

The nested rectangle configuration of the grid probe 34 provides a particular advantage in that it acts to reduce the effective resistance of the wood or paper sample even though the inherent resistivity of the sample may be very high. Additionally, the configuration acts to reduce errors associated with fringing electrical fields because the resistance is measured over the controlled area between the conductors forming the grid probe 34 where the geometry of the electrical fields is well-behaved. This configuration may therefore be placed close to an edge of a sample, or a plurality of such configured grid probes 34 may be utilized to obtain a distributed measurement of moisture content of a sample.

Figure 4:
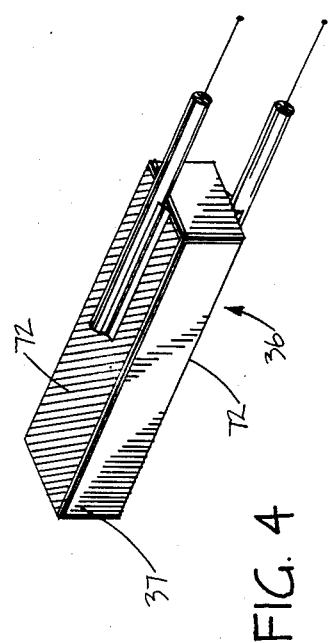
FIG. 4 is a perspective view of a wood and paper sample interposed between two conducting sheets forming an alternate probe of the invention.

Another probe, suitable for use with the resistance-controlled oscillator 13, is a parallel plate probe, indicated generally at 36 in FIG. 4. A parallel plate probe of this type is generally described in Duff, J. E. "A Probe for Accurate Determination of Moisture Content in Wood Products in Use", U.S. Forest Service Research Note, FPL-0142, August 1966, for use with direct current measurement circuits. As discussed in more detail below, the parallel plate probe 36 has been found to operate in connection with both resistive and capacitive embodiments of the present invention. The parallel plate probe 36 is formed on two opposing sides of a thin wood or paperboard sample 37 by placing two conducting elements 72 on the two sides of the sample 37. The parallel plate probe 36 may be connected to the resistance-controlled oscillator 13 as shown schematically in FIG. 6 as resistive probe 39.

Figure 7:
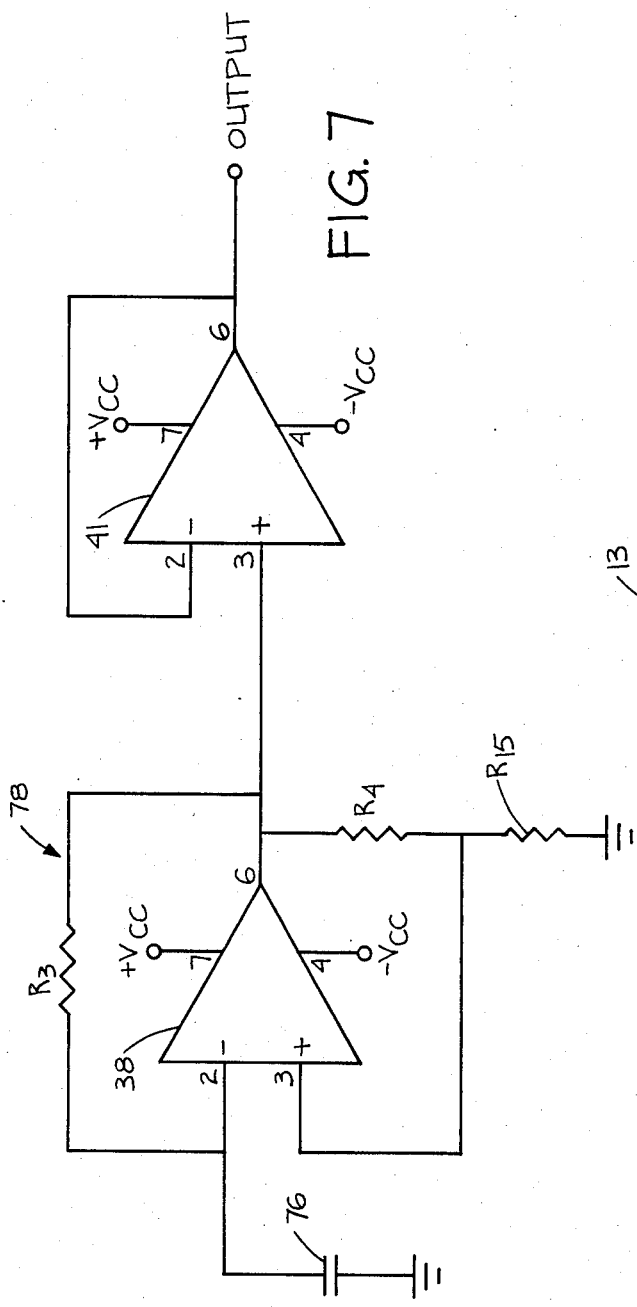
FIG. 7 is an electrical schematic diagram of the capacitance-controlled oscillator circuit used in a preferred embodiment of the invention.

A second preferred embodiment of the invention employs a capacitive probe. The resistance-controlled oscillator circuit 13 (see FIG. 6) is modified, as shown in FIG. 7, by substituting a reference resistor $R_{15}$ for the resistive probe 39 (see FIG. 6), and by replacing the reference capacitor $C_{10}$ with a capacitive probe 76. The resistance-controlled oscillator circuit 13 of the probe transducer circuit 12 may thus be modified so that it is a capacitance-controlled oscillator 78 (see FIG. 7) the frequency of which is dependent upon the capacitance of the capacitive probe 76 when applied to a sample. Capacitive probe 76 could be a probe such as an interflute probe 75 as illustrated in FIG. 5 or probe 36 as illustrated in FIG. 4. The capacitance, like the resistance, of a paperboard sample 80 is functionally related to its moisture content so that the frequency of the capacitance-controlled oscillator circuit 78 is also proportional to the moisture content of the wood or paperboard sample. The frequency-to-voltage conversion circuit 14 and the interface, computational, display, or process control circuits 16 are used in the same manner as in the first preferred embodiment previously described.

As indicated above, one type of capacitive probe 76 used in the second preferred embodiment of the invention is shown in detail in FIG. 5 and depicted generally at 75. The illustrated capacitive probe 75 is formed by inserting a number of conducting rods 82 into flutes 84 of a corrugated paperboard sample 80 and electrically connecting the rods 82 in an alternating manner to the capacitance-controlled oscillator circuit 78. The capacitive effect is enhanced by using more than two rods 82. Additionally, a series of rods 82 produces a more uniform and consistent measuring environment by reducing the effects of fringing electrical fields at the edges of the array of rods 82.

Of course, the probe 36 illustrated in FIG. 4 will also produce a variable capacitance effect dependent upon the moisture content of the sample when connected as a capacitive probe 76 in the capacitance-controlled circuit 78 of FIG. 7.

In the preferred embodiments of the invention as illustrated in the accompanying drawings, the following circuit components are used:

| | |
|---|---|
| $R_1$, $R_3$, $R_8$ | 1 M Ω |
| $R_2$, $R_4$ | 10 M Ω |
| $R_5$, $R_6$ | 100 K Ω |
| $R_7$ | 2.2 K Ω |
| $R_9$ | 200 K Ω |
| $R_{10}$ | 68 K Ω |
| $R_{11}$ | 130 K Ω |
| $R_{12}$ | 120 K Ω |
| $R_{13}$ | 1 K Ω |
| $R_{14}$ | 5.1 K Ω |
| $R_{15}$ | 200 K Ω |
| $R_{16}$, $R_{17}$, $R_{18}$ | 680 Ω |
| $C_1$ | 100 pf |
| $C_2$ | 1000 pf |
| $C_3$, $C_4$, $C_6$ | 0.1 μf (selected for total of 0.2 μf, 1%) |
| $C_5$, $C_8$ | 0.047 μf, mylar |
| $C_7$ | 0.22 μF |
| $C_9$ | 0.022 μF |
| $C_{10}$ | 500 pF |
| Potentiometers 45, 58 | 10 K Ω linear trimpot |
| Potentiometer 50 | 20 K Ω linear trimpot |
| Interstage coupling potentiometers 46, 52 | 100 K Ω linear trimpot |
| Variable gain potentiometer 56 | 500 K Ω linear trimpot |
| BIFET operational amplifier 38 | CA3140; 8 pin to-5 case; (pins 1, 5, 8 are not connected) |
| Operational amplifiers 41, 47, 94 | A 741; 8 pin MINIDIP |
| Astable multivibrator 88 | 555; 8 pin |
| Frequency-to-voltage converter 48 | Teledyne 9400 F/V |
| $I_{c1}$ | INTEL 8216 4-bit parallel bi-directional bus driver, 16 pin dip |
| $I_{c2}$ | INTEL 8216 4-bit parallel bi-directional bus driver, 16 pin dip |
| $I_{c3}$ | INTEL 8216 4-bit parallel bi-directional bus driver, 16 pin dip |
| $I_{c4}$ | INTEL 8216 4-bit parallel bi-directional bus driver, 16 pin dip |
| $I_{c5}$ | SN7485 4-bit magnitude comparators, 16 pin dip |
| $I_{c6}$ | SN7404(J,N) Hex |

| | |
|---|---|
| $I_{c7}$ | Inverters, 14 pin dip SN5430(J,N) 8-input positive-nand gates, 14 pin dip |
| $S_1$ | 4 pole-single-throw dip switch, alco-switch DSS-4 or equivalent |
| $V_{CC}$ | 15 volts DC |
| $V_{DD}$ | +5 volts DC |
| $V_{SS}$ | −5 volts DC |

All resistors are 5%, ¼ watt, carbon resistors and all capacitors, except $C_5$ and $C_8$, are 5%, silver mica, 100 volt capacitors.

The following source program is used with an Apple II ® computer system in combination with the invention:

```
]PRINT CHR$(27)"C"CHR$(55)

]LIST

1  REM   THE PROGRAM "STORE"
2  REM   LOOK AT LINES 800-860
         FOR EXPLANATION
         OF VARIABLES
5  LOMEM: 32000
6  TMIN = -1:AMIN = 2300:FIRST =
         1:MIN = 2501
7  DIM AV(15): DIM AN(15): REM
         VARIABLES USED IN CONTINUOUS
         AVERAGING
8  FOR I = 0 TO 15
9  AN(I) = 0:AV(I) = 0: NEXT I
10 HOME : GOSUB 430
11 PRINT "          *** STORE ***
   ": PRINT : PRINT "THIS PROGR
   AM TAKES DATA FROM THE APPLE
      DATA ACQUISITION SYSTEM AT
      REGULAR        INTERVALS AND
      STORES IT ON DISK IN A    FI
   LE.": PRINT : PRINT
12 INPUT "HOW FREQUENTLY, IN MIN
   UTES, WOULD YOU    LIKE DATA
   TO BE SAMPLED ? ";DI: PRINT
   : INPUT "WHAT DO YOU WANT FO
   R AN AVERAGING          INTERVA
   L WITHIN THE SAMPLING INTERV
   AL    (IN MINUTES) ? ";DA: PRINT
   : IF DA > DI THEN 11
13 D$ = CHR$(4): PRINT D$;"PR#4
   ": PRINT D$;"IN#4": INPUT "
   ";T$: PRINT D$;"PR#0": PRINT
   D$;"IN#0":NAME$ = LEFT$(T$
   ,5) + CHR$(32) + STR$(DI
   ): REM READS TIME FROM APPL
   ECLOCK, SLOT #4. SEE "THE D
   OS MANUAL" PGS. 29-31
14 PRINT "THE NAME OF YOUR DATAF
   ILE FOR TODAY    IS: DATAF
   ILE.";NAME$
15 PRINT : INPUT "WHEN YOU ARE R
   EADY TO BEGIN TYPE IN 'GO' A
   ND RETURN.";G$
20 FAC = 159 / 255:YO = 159:ZERO =
    0
30 LABLE$ = "   0 1 2 3 4 5 6 7
         8 9 A B C D E F"
40 POKE 34,20: HOME : PRINT LABL
   E$: POKE 34,22: HOME : HGR
45 REM   HGR SETS HIGH RESOLUTION
         GRAPHICS MODE FOR THE SCREE
         N. SEE "APPLESOFT" PG. 87
50 HCOLOR= 3: HPLOT 10,0 TO 10,1
   59: FOR M = 159 TO 0 STEP -
   10: HPLOT 5,M TO 15,M: NEXT
55 REM   FOR HCOLOR AND HPLOT SEE
         "APPLESOFT" PGS. 89-90
60 FOR LOOP = 1 TO 2 STEP 0
70 CALL 768
75 REM   READ TIME FROM SLOT #4
80 PRINT D$;"PR# 4"
85 PRINT D$;"IN# 4"
90 INPUT " ";T$
100 PRINT D$;"PR# 0"
105 PRINT D$;"IN# 0"
110 FOR I = 872 TO 887
112 IF MIN < (AMIN) THEN 120
113 REM  TAKE CURRENT VALUES OF
         INPUT AND AVERAGE THEM IN
115 AN(I - 872) = AN(I - 872) + 1
118 AV(I - 872) = (AV(I - 872) *
    (AN(I - 872) - 1) + PEEK(I
    )) / AN(I - 872)
120 P = (I - 872) * 14 + 29
130 Y = YO - FAC * PEEK(I)
140 FOR K = 0 TO 3
150 X = P + K
160 HCOLOR= 0: HPLOT X,YO TO X,Z
    ERO
170 HCOLOR= 3: HPLOT X,YO TO X,Y
180 NEXT K: NEXT I
190 PRINT LEFT$(T$,14)
193 REM  HAS KEYBOARD BEEN TOUCH
         ED?
200 IF PEEK(-16384) > 127 THEN
    LOOP = 2: REM SEE "APPLESOF
    T" PG.130
205 GOSUB 570
210 NUL = PEEK(-16368): NEXT
    LOOP: REM  SEE "APPLESOFT" P
    G. 130
220 TEXT : HOME
230 PRINT "ADAS APPLICATION PROG
    RAM 001"
240 PRINT "OUTPUT SCALED TO 8 BI
    TS"
250 PRINT
260 PRINT "CHANNEL          OUTPUT"
270 PRINT
280 FOR J = 0 TO 15: HTAB(3): PRINT
    J: NEXT
285 REM  FOR HTAB SEE "APPLESOFT
    " PG. 50
290 FOR KK = 1 TO 2 STEP 0
300 CALL 768
310 FOR I = 872 TO 887
312 IF MIN < (AMIN) THEN 320
313 REM  TAKE CURRENT VALUES OF
         INPUT AND AVERAGE THEM IN
315 AN(I - 872) = AN(I - 872) + 1
318 AV(I - 872) = (AV(I - 872) *
    (AN(I - 872) - 1) + PEEK(I
    )) / AN(I - 872)
320 VTAB 6 + I - 872: HTAB(16):
    CALL -868: PRINT PEEK(I
    )
```

```
322 REM  FOR VTAB SEE "APPLESOFT
    " PG.50
330 NEXT I
332 REM  GET VALUE OF TIME FROM
    SLOT #4
333 PRINT D$;"PR# 4"
336 PRINT D$;"IN# 4"
340 INPUT " ";T$
343 PRINT D$;"PR# 0"
346 PRINT D$;"IN# 0"
350 PRINT
360 PRINT "THE DATE AND TIME IS:
    ";
370 T1$ = LEFT$ (T$,8) + CHR$ (
    58) + MID$ (T$,10,2) + CHR$
    (58) + MID$ (T$,13,2)
380 PRINT T1$
390 X1 = FRE (0): REM  SEE "APPL
    ESOFT" PG.53
400 IF PEEK ( - 16384) > 127 THEN
    KK = 2
405 GOSUB 570
410 NIL = PEEK ( - 16368): NEXT
    KK
415 X1 = FRE (0)
420 GOTO 40
425 REM  FOR LINES 430-550  SEE
    "         APPLESOFT" APP
    ENDIX J
430 POKE 768,162: POKE 769,0: POKE
    770,142: POKE 771,35: POKE 7
    72,194: POKE 773,160: POKE 7
    74,15: POKE 775,152: POKE 77
    6,234:
440 POKE 777,234: POKE 778,234: POKE
    779,9: POKE 780,80: POKE 781
    ,41: POKE 782,95: POKE 783,1
    41: POKE 784,32: POKE 785,19
    4:
450 POKE 786,162: POKE 787,64: POKE
    788,142: POKE 789,32: POKE 7
    90,194: POKE 791,44: POKE 79
    2,32: POKE 793,194: POKE 794
    ,16:
460 POKE 795,251: POKE 796,169: POKE
    797,96: POKE 798,141: POKE 7
    99,32: POKE 800,194: POKE 80
    1,173: POKE 802,33: POKE 803
    ,194:
470 POKE 804,153: POKE 805,104: POKE
    806,3: POKE 807,142: POKE 80
    8,32: POKE 809,194: POKE 810
    ,136: POKE 811,16: POKE 812,
    218:
480 POKE 813,96: POKE 814,169: POKE
    815,64: POKE 816,141: POKE 8
    17,32: POKE 818,194: POKE 81
    9,169: POKE 820,127: POKE 82
    1,141:
490 POKE 822,34: POKE 823,194: POKE
    824,96: POKE 825,160: POKE 8
    26,64: POKE 827,162: POKE 82
    8,0: POKE 829,173: POKE 830,
    79:
500 POKE 831,0: POKE 832,141: POKE
    833,33: POKE 834,194: POKE 8
    35,169: POKE 836,255: POKE 8
    37,141: POKE 838,35: POKE 83
    9,194:
510 POKE 840,142: POKE 841,32: POKE
    842,194: POKE 843,140: POKE
    844,32: POKE 845,194: POKE 8
    46,96: POKE 847,0: POKE 848,
    172:
520 POKE 849,100: POKE 850,3: POKE
    851,173: POKE 852,101: POKE
    853,3: POKE 854,153: POKE 85
    5,16: POKE 856,194: POKE 857
    ,96:
530 POKE 858,172: POKE 859,102: POKE
    860,3: POKE 861,185: POKE 86
    2,16: POKE 863,194: POKE 864
    ,141: POKE 865,103: POKE 866
    ,3:
540 POKE 867,96: POKE 868,0: POKE
    869,0: POKE 870,0: POKE 871,
    0: POKE 872,0:
550 CALL 814
560 RETURN
570 REM WRITE-IN-FILE SUBROUTINE
    CHECKS THE TIME TO SEE IF A
    RECORD NEEDS TO BE RECORDED,
    IF SO PREPARES DATA FOR
    RECORDING AND RECORDS IT IN
    FILE.
580 V$ = MID$ (T$,7,2) + MID$ (
    T$,10,2)
590 VMIN = VAL ( RIGHT$ (V$,2)):
    REM   GIVES WHAT MINUTE
600 VHR = VAL ( LEFT$ (V$,2)): REM
    GIVES WHAT HOUR
610 MIN = VHR * 60 + VMIN
612 REM  CHECK IF MINUTE HAS PAS
    SED
614 IF MIN = (TMIN) THEN  RETURN
616 TMIN = MIN
620 REM  CHECK FOR MULTIPLES OF
    RECORDING INTERVAL.  RECORDS
    ARE MADE AT ANY INTEGER
    MULTIPLE OF MINUTES FROM
    ZERO.
630 VI = INT (MIN / DI)
632 IF MIN - VI * DI > 0 THEN  RETURN
635 REM COMBINE DATA INTO SINGLE
    CHARACTER STRING FOR
    RECORDING
640 B$ = " ":D$ = CHR$ (4)
645 FOR I = 872 TO 887
650 C$ = CHR$ (47) + STR$ ( INT
    (AV(I - 872) + 0.5))
655 B$ = B$ + C$
660 NEXT I
665 A$ = LEFT$ (T$,11) + B$
670 REM RECORD DATA. SEE "DOS MA
    NUAL" PGS. 82-89
675 NUMBER = VAL (V$): REM
    12:20=1220
680 NAME$ = LEFT$ (T$,5) + CHR$
    (32) + STR$ (DI)
685 PRINT D$;"OPEN DATAFILE.";NA
    ME$;",L90,D2"
686 IF FIRST = 1 THEN 688
687 IF VAL (V$) < > DI THEN 69
    0
688 FIRST = 0: PRINT D$;"WRITE DA
    TAFILE.";NAME$;",R2401": PRINT
    DI
689 PRINT D$;"WRITE DATAFILE.";N
    AME$;",R2402": PRINT DA
690 PRINT D$;"WRITE DATAFILE.";N
    AME$;",R";NUMBER
695 PRINT A$
700 PRINT D$;"CLOSE DATAFILE.";N
    AME$
705 REM  RESET AVERAGING ARRAYS
```

```
707  IF MIN + DI > 2400 THEN MIN =
     0
708  AMIN = MIN + DI - DA
710  FOR I = 0 TO 15
715  AN(I) = 0:AV(I) = 0: NEXT I
720  REM  RESET DEFAULT TO DISK 1

725  PRINT D$;"OPEN DUMMYFILE, D1
     "
730  RETURN
735  REM  END OF WRITE-IN-FILE SU
     BROUTINE
800  REM  EXPLANATION OF
                VARIABLES
802  REM  TMIN : TEMPORARY VALUE
                OF MINUTE
804  REM  AMIN : VALUE OF MINUTE
                AT WHICH AVER-
                AGING BEGINS
806  REM  FIRST : INDICATES IF
                FIRST TIME FOR
                A NEW FILE
808  REM  MIN : VALUE OF MINUTE
810  REM  AN(I) : NUMBER OF DATA
                POINTS BEING
                AVERAGED
812  REM  AV(I) : AVERAGE SO FAR
                COMPUTED
814  REM  DI : SAMPLING INTERVAL
816  REM  DA : AVERAGING INTERVAL

818  REM  D$ : CONTROL D
820  REM  T$ : DATE AND TIME FROM
                APPLECLOCK
822  REM  NAME$ : DATE & SAMPLING
                INTERVAL PART
                OF FILENAME
                E.G. 10/01 1
824  REM  G$ : DUMMY VARIABLE
826  REM  FAC : SCALING FACTOR
                FOR HEIGHT OF
                BARS
828  REM  Y0 : LONGEST BAR LENGHT

830  REM  LABLE$ : LABLE BELOW
                BARS
832  REM  P : OFFSET FACTOR FOR
                X-COORDINATE
                VALUE IN BAR
                GRAPH DISPLAY
834  REM  Y : Y-COORDINATE
836  REM  X : X-COORDINATE
838  REM  NUL : DUMMY VARIABLE
840  REM  T1$ : SHORTENED VERSION
                OF T$ (NO SECONDS)
842  REM  X1 : DUMMY VARIABLE
844  REM  NIL : DUMMY VARIABLE
846  REM  V$ : CONCATENATION OF
                HOUR AND MINUTE
848  REM  VMIN : VALUE OF MINUTE
                FROM T$ (<60)
850  REM  VHR : VALUE OF HOUR
                FROM T$
852  REM  VI : INTEGER NUMBER OF
                TIMES THAT THE
                SAMPLING INTERVAL
                GOES INTO HOURS *
                60 + MINUTES
854  REM  B$ : CONCATENATION OF
                ALL 16 CHANNELS
                SEPARATED BY "/"
856  REM  C$ : CONCATENATION OF A
                "/" + THE AVERAGE
                OF ONE CHANNEL
858  REM  A$ : CONCATENATION OF
                DATE, TIME, AND B$

860  REM  NUMBER : VALUE OF V$
870  END

]NEW

]LOAD RECALL
]LIST

1    REM  THIS IS THE PROGRAM
                "RECALL"
2    REM  FOR EXPLANATION OF
                VARIABLES SEE
                LINES 1100-1146
5    PRINT : PRINT "              ***
                RECALL   ***": PRINT : PRINT
     "THIS PROGRAM WILL PULL THE
     DATA STORED  BY THE A.D.A.S.
     OFF THE DISK."
10   D$ = CHR$ (4): REM  SEE "DOS
     MANUAL" PGS. 29-31
15   PRINT D$;"CATALOG D2"
20   PRINT : PRINT "IN THE FORM BE
     LOW, TYPE IN THE FILENAME FO
     R THE DAY IT WAS RUN.": PRINT
30   PRINT "     DATAFILE.XX/XX X":
     PRINT
40   INPUT "     DATAFILE.";Q$: PRINT

50   REM  CHECK FOR PLAUSIBLE INPU
     T
65   REM  CHECK FOR VALID LENGTH
70   IF  LEN (Q$) < 7 THEN 10
75   REM  CHECK FOR VALID MONTH
80   IF  VAL ( LEFT$ (Q$,2)) > 12 THEN
     10
90   IF  VAL ( LEFT$ (Q$,2)) < 1 THEN
     10
95   REM  CHECK FOR VALID DAY
100  IF  VAL ( MID$ (Q$,4,2)) < 1
     THEN 10
110  IF  VAL ( MID$ (Q$,4,2)) > 3
     1 THEN 10
120  IF  MID$ (Q$,3,1) < > CHR$
     (47) THEN 10: REM  CHR$(47)=
     "/"
130  GOSUB 900: REM  READ FROM FI
     LE THE SAMPLING AND AVERAGIN
     G INTERVALS
140  GOSUB 1005: REM  SET SCANNIN
     G RATE
150  PRINT : PRINT "TYPE IN THE T
     IME AT WHICH YOU WOULD LIKE
     TO BEGIN EXAMINING DATA.": PRINT

160  INPUT "HOUR:  ";HOUR: PRINT
     : INPUT "MINUTE: ";MIN
170  DI = 0
180  II = 0
200  REM  READING FILE
210  PRINT "HOW MANY HOURS AND MI
     NUTES WORTH OF DATA DO YOU W
     ISH TO SEE?": PRINT
220  INPUT "HOURS:  ";IHOUR: PRINT

230  INPUT "MINUTES: ";IMIN: PRINT
```

```
240 ND = INT ((HOUR * 60 + MIN) *
    SC / DI) * DI / SC
242 START = 100 * INT (ND / 60) +
    ND - ( INT (ND / 60) * 60)
252 JNUM = HOUR * 60 + MIN + IHOU
    R * 60 + IMIN
254 MD = INT (JNUM / DI) * DI
256 FINISH = 100 * INT (MD / 60)
    + MD - ( INT (MD / 60) * 60
    ) - O1
258 O2 = 0: REM  FIRST PASS THROU
    GH LOOP
259 IF START > 2359 THEN START =
     2400: REM  IF START IS GREAT
    ER.THAN 2359 THEN NEED TO GO
     TO NEXT DAY'S FILE.
260 FOR I = START TO FINISH STEP
     DI
268 REM  ACCOUNT FOR CROSSING
    THE INTERVAL 61-99
270 DD = INT (DI / 60)
271 DL = DI - DD * 60
272 IF O2 = 1 THEN I = I + 40 *
    DD: REM   ADD 40 MINUTES FOR
    EVERY STEP OF AN HOUR IF NO
    T FIRST PASS THROUGH LOOP
273 IF O2 = 1 THEN IF  VAL ( RIGHT$
    ( STR$ (II),2)) + DL > 59 THEN
     I = I + 40: REM   ADD 40 MIN
    UTES IF ON A NEW HOUR AND IF
     FIRST PASS THROUGH LOOP
274 IF I > FINISH THEN 730
275 REM  MAKE SURE NOT NEW.DAY,
    IF IT IS A NEW DAY OPEN NEXT
     DAY'S FILE
280 IF I < 2400 GOTO 340
290 PRINT : PRINT "INPUT
    THE DAY AFTER "; LEFT$ (O$,
    5): PRINT "IN THE FORM XX/XX
    ": PRINT "SAMPLING INTERVAL
    MUST BE ": PRINT "THE SAME F
    OR BOTH DAYS."
295 INPUT " ";O$:O$ = O$ + CHR$
    (32) + STR$ (DI / SC)
296 GOSUB 900: REM   READ FROM F
    ILE THE SAMPLING AND AVERAGI
    NG INTERVALS
300 GOSUB 1000: REM   SET SCANNI
    NG RATE
315 START = 0
320 HOUR = HOUR - 24
325 GOTO 252
330 REM  FOR USING RANDOM-ACCESS
     TEXT FILES SEE "DOS MANUAL"
     PG.82-99
340 PRINT D$;"OPEN DATAFILE.";O$
    ;",L80,D2"
350 PRINT D$;"READ DATAFILE.";O$
    ;",R";I
360 INPUT A$
370 PRINT D$;"CLOSE DATAFILE.";O
    $
380 HOME
385 REM  CHECK A$ FOR BEING VALI
    D
390 IF  LEN (A$) < 41 GOTO 410
400 DTETIME$ = O$ + CHR$ (32) +
    LEFT$ ( STR$ (I),2) + CHR$
    (58) + RIGHT$ ( STR$ (I),2)
410 PRINT : PRINT "INVALID RECOR
    D READING": PRINT "FOR";DTET
    IME$
420 GOTO 670
440 REM  PRINT DATA
450 PRINT "DATA RECALLED FROM AD
    A$": PRINT "OUTPUT SCALED TO
     8 BITS": PRINT : PRINT "CHA
    NNEL    OUTPUT": PRINT
460 L = 10: REM  L AND L1 ARE THE
     NUMBER OF CHARACTERS OVER
    FROM THE LEFT IN A$.
465 REM  LOOK FOR FIRST SLASH IN
     A$
470 IF  MID$ (A$,L,1) = "/" THEN
     500
480 L = L + 1
490 GOTO 470
500 L = L + 1: REM   ADVANCE L ONE
     MORE (FIRST CHARACTER AFTER
     SLASH)
510 FOR K = 0 TO 15
520 HTAB (4): PRINT K;
525 REM  FOR HTAB SEE "APPLESOFT
    " PG.50
530 L1 = L
540 IF K = 15 THEN 630: REM   LAS
    T CHANNEL'S DATA, PRINT REST
     OF A$ FROM RIGHT OF LAST SL
    ASH
545 REM  FIND NEXT SLASH AND PRI
    NT WHAT IS BETWEEN SLASHS
550 IF  MID$ (A$,L1,1) = "/" THEN
     580
560 L1 = L1 + 1: REM    ADVANCE
    L ONE MORE (FIRST CHARACTER
    AFTER SLASH)
570 GOTO 550
580 HTAB (17): PRINT  MID$ (A$,L
    ,L1 - L);
590 PRINT
600 L = L1 + 1
610 NEXT K
620 GOTO 650
630 HTAB (17): PRINT  MID$ (A$,L
    )
640 GOTO 610
650 TIME$ =  LEFT$ (A$,8) + CHR$
    (58) + MID$ (A$,10,2)
660 PRINT : PRINT : PRINT "THE D
    ATE AND TIME IS:  ";TIME$
670 REM  SPACE BAR PAUSE
680 PRINT : PRINT "PRESS SPACEBA
    R TO CONTINUE."
685 REM  FOR LINES 690-710 SEE "
    APPLESOFT" PG. 130
690 S =  PEEK ( - 16384)
700 IF S < 127 THEN 690
710 POKE  - 16368,0
720 II = I
725 O2 = 1: REM  NOT FIRST PASS T
    HROUGH LOOP
730 NEXT I
740 O1 = 1
800 PRINT : INPUT "WOULD YOU LIK
    E TO EXAMINE THE DATA THAT I
    MMEDIATELY FOLLOWS THE LAST
    OUTPUTTED DATA?";Y$
810 IF  LEFT$ (Y$,1) < > "Y" THEN
     832
```

```
820 HOUR = INT (II / 100)
822 MIN = II - INT (II / 100) *
    100 + DI
830 GOTO 210
832 PRINT : INPUT "WOULD YOU LIK
    E TO EXAMINE THE DATA THAT I
    MMEDIATELY FOLLOWS THE LAST
    OUTPUTTED DATA WITH A DIFFE
    RENT SCANNING RATE? ";Y3$
834 IF LEFT$ (Y3$,1) < > "Y" THEN
    840
835 DI = DI / SC
836 GOSUB 1000: REM SET SCANNIN
    G RATE
838 GOTO 820
840 PRINT : PRINT "IS ANY MORE D
    ATA NEEDED FROM": PRINT "DAT
    AFILE.";Q$;"? ": INPUT " ";Y
    1$
850 IF LEFT$ (Y1$,1) = "Y" THEN
    130
860 PRINT : INPUT "DO YOU WISH T
    O EXAMINE A DIFFERENT    D
    ATAFILE?";Y2$
870 IF LEFT$ (Y2$,1) = "Y" THEN
    15
875 REM RESET DEFAULT TO DISK 1
880 PRINT D$;"OPEN DUMMYFILE,D1"
890 END
895 REM READ FROM FILE SAMPLING
    AND AVERAGING INTERVALS SUB
    ROUTINE
900 PRINT D$;"OPEN DATAFILE.";Q$
    ;",L80,D2"
910 PRINT D$;"READ DATAFILE.";Q$
    ;",R2401": INPUT DI
920 PRINT D$;"READ DATAFILE.";Q$
    ;",R2402": INPUT DA
930 PRINT D$;"CLOSE DATAFILE.";Q
    $
940 PRINT "FOR THIS FILE:": PRINT
    "THE SAMPLING INTERVAL IS ";
    DI
950 PRINT "THE AVERAGING INTERVA
    L IS ";DA
960 RETURN
1000 REM SCAN SUBROUTINE
1005 PRINT : PRINT "INPUT THE MU
     LTIPLE OF THE": PRINT "SAMPL
     ING INTERVAL AT WHICH": INPUT
     "YOU WOULD LIKE TO SCAN? ";S
     C
1010 SC = INT (SC)
1020 DI = DI * SC
1030 RETURN
1100 REM      EXPLANATION OF
              VARIABLES
1102 REM  D$ : CONTROL D, SEE
              "DOS MANUAL"
1104 REM  Q$ : DATE AND SAMPLING
              INTERVAL PART OF
              FILENAME
1106 REM  HOUR : VALUE OF HOUR
              WITH WHICH ONE
              BEGINS
              EXAMINING DATA
1108 REM  MIN : VALUE OF MINUTE
              WITH WHICH ONE
              BEGINS
              EXAMINING DATA
1110 REM  O1 : VARIABLE USED IF
              DATA AT INITIAL
              EXAMINATION POINT
              NEEDS TO BE SHOWN
1112 REM  IHOUR : NUMBER OF
              HOURS
              EXAMINING
1114 REM  IMIN : NUMBER OF
              MINUTES
              EXAMINING
1116 REM  DI : SAMPLING INTERVAL
1118 REM  SC : SCANNING RATE
1120 REM  ND : INTEGER NUMBER OF
              TIMES THE SAMP-
              LING INTERVAL
              DIVIDES INTO
              60 * HOUR + MIN
1122 REM  START : FIRST RECORD
              TO BE EXAMINED
1124 REM  JNUM : HOUR * 60 + MIN
              + IHOUR * 60 +
              IMIN
1126 REM  MD : INTEGER NUMBER OF
              TIMES THE PRODUCT
              OF THE SCANNING
              RATE AND SAMPLING
              INTERVAL DIVIDES
              INTO JNUM
1128 REM  FINISH : LAST RECORD
              TO BE
              EXAMINED
1129 REM  O2 : INDICATES IF
              FIRST PASS
              THROUGH LOOP
1130 REM  DD : INTEGER NUMBER OF
              HOURS IN DI
1131 REM  DL : DI - DD * 60
1132 REM  A$ : DATA STRING READ
              FROM RECORD
1133 REM  DTETIME$ : DATE & TIME
1134 REM  L : NUMBER OF CHARACT-
              ERS FROM LEFT
              IN A$
1136 REM  L1 : TEMPORARY VALUE
              OF L
1138 REM  TIME$ : DATE AND TIME
1140 REM  S : DUMMY VARIABLE
              USED TO INDICATE
              KEYBOARD BEING
              TOUCHED
1142 REM  II : LAST VALUE OF
              LOOP COUNTER I
1144 REM  Y$,Y1$,Y2$,Y3$ :
              ANSWERS TO YES
              OR NO PROMPTS
1146 REM  DA : AVERAGING
              INTERVAL
```

It should be clear from the foregoing description of the two preferred embodiments that other mechanical or electrical means could be employed in accomplishing the broad purposes of the invention. It should be understood this description is intended to illustrate but not to limit the scope of the invention as defined in the following claims.

I claim:

1. A method for measuring the moisture content of wood or paper products comprising the steps of:

(a) forming a substantially two-dimensional resistive element on a single surface of the product, said resistive element having an inner portion and an outer portion spaced outwardly from and surrounding the inner portion;
(b) completing a resistance-controlled oscillator circuit by electrically attaching the inner and outer portions of the resistive element into said circuit;
(c) generation by the resistance-controlled oscillator circuit of an output signal the frequency of which is dependent upon the resistance of the resistive element;
(d) converting said resistance-dependent output signal of the oscillator circuit to a frequency-dependent direct current voltage level, and
(e) initiating a response to said direct current voltage level according to a predetermined relationship between said direct current voltage level and the moisture content of the wood or paper product.

2. The method as defined in claim 1, wherein:
(a) said resistance-controlled oscillator circuit inherently generates said output signal having a frequency proportional to the logarithm of the resistance of the resistive element.

3. The method as defined in claim 2, wherein:
(a) the frequency of said output signal is related to the logarithm of the resistance of the resistive element according to the following formula $$\text{Frequency} = A[\ln(1 + BR_x)]^{-1}$$

where $R_x$ is the resistance of the resistive element and A and B are constants determined by the elements of the resistance-controlled oscillator circuit.

4. A method as defined in claim 1, in which the step of forming a resistive element comprises:
(a) Applying directly upon the surface of the wood or paper product a contact grid pattern using an electrically conductive substance, which pattern consists of two spaced conducting elements.

5. A method as defined in claim 1, in which the step of completing the oscillator circuit comprises:
(a) Forming a resistance-controlled oscillator circuit which responds logarithmically to the resistance of said resistive element, including a BIFET operational amplifier and associated circuitry such that the circuit, including the wood or paper product sample, oscillates at a frequency of between 300 Hertz and 5000 Hertz.

6. A method as defined in claim 1, in which the step of initiating a response comprises:
(a) Determining the level of said direct current voltage,
(b) Converting said voltage level into a generally corresponding humidity value, and
(c) Communicating said humidity value in a humanly-intelligible form.

7. A method as defined in claim 1, in which the step of initiating a response comprises:
(a) Actuating humidity control apparatus when said direct current voltage level exceeds or falls short of a preestablished voltage.

8. A method of measuring the moisture content of wood or paper products having fluted interior cavities, comprising the steps of:
(a) inserting a plurality of appropriately sized cylindrical conducting electrodes into a corresponding plurality of adjacent fluted cavities of the wood or paper product;
(b) electrically connecting alternating electrodes to provide at least two electrical attachment sites;
(c) completing a capacitance-controlled oscillator circuit by incorporating the capacitive element through said attachment sites into said circuit to generate an output frequency dependent upon the capacitance of the capacitive element;
(d) converting said capacitance-dependent frequency of the oscillator to a frequency-dependent direct current voltage level; and
(e) initiating a response to said direct current voltage level based on a predetermined relationship between said direct current voltage level and the moisture content of the wood or paper product.

9. Apparatus for measuring the moisture content of wood or paper products, comprising:
(a) an impedance probe element formed from a portion of the product, and wherein said impedance probe element is a substantially two-dimensional resistive element formed on a single surface of the product, said resistive element having an inner portion and an outer portion spaced outwardly from and surrounding said inner portion;
(b) at least one electrical attachment site on each of said portions;
(c) a resistance-controlled oscillator circuit, having a resistive element and a capacitive element, formed by incorporating said probe element as one of said resistive and capacitive elements into said circuit at said attachment sites to generate an output signal the frequency of which is dependent upon the impedance of said probe element;
(d) a frequency-to-voltage conversion circuit for converting said output signal of said oscillator circuit to a frequency-dependent direct current voltage level; and
(e) means for initiating a response to said direct current voltage level according to a predetermined relationship between said direct current voltage level and the moisture content of the product.

10. Apparatus as defined in claim 9 for measuring the moisture content of wood and paper products in which said resistive element comprises:
(a) A contact grid pattern of electrically conducting materials directly applied to the surface of the wood or paper product, which pattern consists of two spaced conducting elements.

11. Apparatus as defined in claim 10, wherein:
(a) said two spaced conducting elements are a central conducting element and an outer conducting element spaced generally equidistantly from said central element.

12. Apparatus as defined in claim 9 for measuring the moisture content of wood or paper products in which said responsive means comprises:
(a) Means for determining the level of said direct current voltage,
(b) Means for converting said voltage level into a generally corresponding humidity value, and
(c) Means for communicating said humidity value in a humanly intelligible form.

13. Apparatus as defined in claim 9 for measuring the moisture content of wood or paper products in which said responsive means comprises:

(a) Means for actuating humidity control apparatus when said direct current voltage level exceeds or falls short of a preestablished voltage.

14. Apparatus for measuring the moisture content of wood or paper products having fluted interior cavities, comprising:
 (a) a plurality of appropriately sized generally cylindrical, electrically conductive electrodes inserted into a corresponding plurality of adjacent fluted cavities of the wood or paper product, said conductive electrodes electrically connected to one another in alternating sequence;
 (b) a capacitance-controlled circuit incorporating the capacitive element and which generates an output signal the frequency of which is dependent upon the capacitance of the capacitive element;
 (c) a frequency-to-voltage conversion circuit for converting the output signal of the oscillator into a frequency-dependent direct current voltage level proportional to said output frequency of the oscillator; and
 (d) means responsive to said direct current voltage level based upon a predetermined relationship between said direct current voltage level and the moisture content of the wood or paper product.

* * * * *